(12) United States Patent
Van Der Wijk et al.

(10) Patent No.: US 12,253,577 B2
(45) Date of Patent: Mar. 18, 2025

(54) RAPID MAGNETIC BIOSENSOR

(71) Applicant: SIEMENS HEALTHINEERS NEDERLAND B.V., The Hague (NL)

(72) Inventors: Thea Van Der Wijk, Bunnik (NL); Menno Willem Jose Prins, Rosmalen (NL); Richard Joseph Marinus Schroeders, Eindhoven (NL)

(73) Assignee: Siemens Healthineers Nederland B.V., The Hague (NL)

( * ) Notice: Subject to any disclaimer, the term of this patent is extended or adjusted under 35 U.S.C. 154(b) by 301 days.

(21) Appl. No.: 17/377,586

(22) Filed: Jul. 16, 2021

(65) Prior Publication Data

US 2021/0341554 A1 Nov. 4, 2021

Related U.S. Application Data

(62) Division of application No. 12/299,781, filed as application No. PCT/IB2007/051698 on May 7, 2007, now abandoned.

(30) Foreign Application Priority Data

May 10, 2006 (EP) .................................. 06113763

(51) Int. Cl.
*G01N 27/74* (2006.01)
*B82Y 25/00* (2011.01)
(Continued)

(52) U.S. Cl.
CPC .............. *G01R 33/02* (2013.01); *B82Y 25/00* (2013.01); *G01N 27/745* (2013.01);
(Continued)

(58) Field of Classification Search
CPC .. G01R 33/02; G01R 33/0213; G01R 33/093; G01R 33/12; G01R 33/1269;
(Continued)

(56) References Cited

U.S. PATENT DOCUMENTS

| 4,336,173 A | 6/1982 | Ugelstad |
| 4,459,378 A | 7/1984 | Ugelstad |

(Continued)

FOREIGN PATENT DOCUMENTS

| DE | 10137665 A1 | 11/2002 |
| WO | 2005010542 A2 | 2/2005 |

(Continued)

OTHER PUBLICATIONS

Ferreira H.A. et al.; Rapid DNA hybridization based on ac field focusing of magnetically labeled target DNA, Applied Physics Letter, AIP, America Institute of Physics, Melville, NY, US, vol. 87, No. 1, Jun. 29, 2005, pp. 13901-13903, XP012075538 ISSN: 003-6951 cited in the application.

(Continued)

*Primary Examiner* — Rebecca M Fritchman
(74) *Attorney, Agent, or Firm* — Dugan & Dugan, PC (57) ABSTRACT

The present invention relates to methods and (bio)sensor systems. Herein, magnetic fields are applied in order to transport magnetic particles laterally over a sensor surface with analyte specific probes. The methods of the invention allow the specific binding of magnetic particles to the sensor surface, while aspecific and unbound particles are removed.

19 Claims, 3 Drawing Sheets

(51) Int. Cl.
*G01N 33/543* (2006.01)
*G01R 33/02* (2006.01)
*G01R 33/09* (2006.01)
*G01R 33/12* (2006.01)
*G01N 35/00* (2006.01)

(52) U.S. Cl.
CPC ... *G01N 33/54333* (2013.01); *G01R 33/0213* (2013.01); *G01R 33/093* (2013.01); *G01R 33/12* (2013.01); *G01R 33/1269* (2013.01); *G01N 35/0098* (2013.01)

(58) Field of Classification Search
CPC .............. B82Y 25/00; G01N 27/745; G01N 33/54333; G01N 35/0098
See application file for complete search history.

(56) References Cited

U.S. PATENT DOCUMENTS

| | | | |
|---|---|---|---|
| 4,654,267 A | 3/1987 | Ugelstad et al. | |
| 5,445,971 A | 8/1995 | Rohr | |
| 6,180,418 B1 | 1/2001 | Lee | |
| 6,548,311 B1 | 4/2003 | Knoll | |
| 6,736,978 B1 | 5/2004 | Porter et al. | |
| 2002/0060565 A1* | 5/2002 | Tondra | G01R 33/1269 324/260 |
| 2003/0041440 A1 | 3/2003 | Shonai | |
| 2004/0009614 A1 | 1/2004 | Ahn et al. | |
| 2004/0115709 A1* | 6/2004 | Morozov | G01N 33/561 436/526 |
| 2005/0087000 A1* | 4/2005 | Coehoorn | C12Q 1/6825 73/53.01 |
| 2005/0127916 A1 | 6/2005 | Tondra | |
| 2007/0264159 A1 | 11/2007 | Graham et al. | |

FOREIGN PATENT DOCUMENTS

| | | |
|---|---|---|
| WO | 2005010543 A1 | 2/2005 |
| WO | 2005116661 A1 | 12/2005 |
| WO | 2006018811 A1 | 2/2006 |
| WO | 2006067747 A2 | 6/2006 |
| WO | 2006079998 A1 | 8/2006 |
| WO | 2006134546 A2 | 12/2006 |
| WO | 2007077498 A1 | 7/2007 |

OTHER PUBLICATIONS

Perrin A. et al.; Immunomagnetic concentration of antigens and detection based on a scanning force microscopic Immunoassay Journal of Immunological Methods, Elsevier Science Publishers B.V., Amsterdam, NL, vol. 224, No. 1-2, Apr. 22, 1999, pp. 77-87, XP004165512 ISSN: 0022-1759 cited in the application.

Edelstein R L, et al.; The Barc Biosensor Applied to the Detection of Biological Warfare Agents Biosensors & Bioelectronics, Elsevier Science Publishers, Barking, GB, vol. 14, No. 10-11, Jan. 2000, pp. 805-813, XP001069427 ISSN: 0956-5663.

Li Guanxiong, et al.; Detection of single micron-sized magnetic bead and magnetic nanoparticles using spin valve sensors for biological applications": Journal of Applied Physics, American Institute of Physics. New York, US, vol. 93, No. 10, May 15, 2003, pp. 7557-7559, XP012058215 ISSN: 0021-8979.

Luxton R et al. Use of External Magnetic Fields to Reduce Reaction Times in an Immunoassay Using Micrometer-Sized Paramagnetic Particles as Labels (Magnetoimmunoassay) Analytical Chemistry, American Chemical Society. Columbus, US, vol. 76, No. 6, Mar. 15, 2004, pp. 1715-1719, XP001196657 ISSN: 0003-2700 cited in the application.

Dufva, Martin "Fabrication of High Quality Microarrays", Biomolecular Engineering, vol. 22, 2005, pp. 173-184.

Angenendt, Philip et al.; "Toward Optimized Antibody Microarrays: A Comparison of Current Microarray Support Materials", Analytical Biochemistry, vol. 309, 20025 pp. 253-260.

Morozov, Victor N. "Active Bead-Linked Immunoassay on Protein Microarrays", Analytica Chimica Acta, 564, 2006, pp. 40-52.

* cited by examiner

RAPID MAGNETIC BIOSENSOR

CROSS-REFERENCE TO RELATED APPLICATIONS

The present application is a Divisional Application of U.S. Application Ser. No. 12/299,781, entitled "RAPID MAGNETIC BIOSENSOR", filed on Nov. 6, 2008. U.S. application Ser. No. 12/299,781 claims priority to European Patent Application No. 06113763.4, entitled "RAPID MAGNETIC BIOSENSOR", filed on May 10, 2006. The entire contents of each of the above-identified applications are hereby incorporated by reference for all purposes.

The present invention relates to systems, apparatus and methods for detecting and/or quantifying molecules in a sample using magnetic particles, including disposable cartridges for use with such systems as well as to systems and methods for moving such magnetic particles.

The use of magnetic particles in bioassays and biosensors has several attractive aspects. Magnetic particles with analytes can be stirred using magnetic fields which shortens reaction times between probes and analytes. Magnetic fields can be used to remove aspecific bound analytes from a probe, to concentrate magnetic particles in a part of a reaction chamber, or to move particles in and/or out of a reaction chamber. The magnetic properties of magnetic particles themselves can be used for detection purposes.

The type of magnetic field gradients that are generally used are applied perpendicular to a sensor surface to move particles to or from the sensor surface. Also conical fields have been applied to concentrate particles to one particular point, e.g. the objective a microscope. Circular or random magnetic fields are used to create a stirring effect. Examples hereof are described in U.S. Pat. Nos. 5,445,971, 6,548,311, 6,180,418, Perrin et al. (1999), J. Immun. Meth. 224, 77-87; Luxton et al. (2004) Anal. Chem. 76, 1715-1719; and Ferreira et al. (2005) Appl. Phys Lett. 87, 013901.

Nevertheless, devices which would allow the different assay steps to be performed in a faster and more efficient way are highly desirable, more particularly in the context of high throughput screening and on site analysis.

It is an object of the present invention provide alternative or improved systems and methods for detecting and/or quantifying molecules in a sample using magnetic particles as well as disposable cartridges for use with such systems and systems and methods for moving such magnetic particles.

In one aspect, the present invention relates to a system comprising a reaction chamber having a sensor surface and at least one region outside said sensor surface and further comprising at least one means for generating one or more magnetic fields, wherein the at least one means for generating one or more magnetic fields are placed such that one of said magnetic fields has a gradient with a component that is parallel to said sensor surface and spans said sensor surface and said at least one region outside the sensor surface, In addition the one of said magnetic fields can have a gradient with a component perpendicular to said sensor surface wherein said perpendicular component is directed from the reaction chamber to the sensor surface. In the system the magnetic field can be arranged to move magnetic particles laterally over the sensor surface, i.e. along the surface, to a first region outside the sensor surface. In the system, the magnetic field can move magnetic particles from a first region outside the sensor surface, laterally over the sensor surface to a second region outside the sensor surface.

It is possible to have a magnetic field applied only in one direction whereby the particles also move in one direction under the magnetic field. It its simplest version the magnetic field is applied once.

Optionally this process can be repeated by alternating the application of the magnetic field with for example a fluid flow which redirects the magnetic particles to their initial position, i.e. the particles move or flow in two directions, one being the reverse of the other. In this case the magnetic field is applied once followed by a flow of the particles. Alternatively, the magnetic field may be reversed and/or cycled in this manner to move particles back and forth.

By reversing the magnetic field or combining magnetic fields with other forces the first and second regions outside the sensor surface as describe above are the same.

A system can be provided wherein a dedicated area is provided on a region outside the sensor surface for the application of magnetic particles. When these particles are applied in the same plane of the sensor surface, there is no need for a magnetic field that attracts magnetic particles perpendicularly to the sensor surface. Thus, it is possible to design systems wherein magnetic field generators such as current carrying conductors suitable for attracting particles to the sensor surface (5) or to a region (6) outside the sensor surface (5) are absent.

The system of the current invention can comprise inlet means for introducing said magnetic particles into the reaction chamber.

In particular embodiments one or more means for generating a magnetic field comprise two magnets which are located at opposite sides of the sensor surface. In any such system according to the present invention magnetic fields can be applied during a given time period wherein the transport of the magnetic particles transports is larger that the distance obtained by Brownian motion.

In certain embodiments the at least one means for generating one or more magnetic fields is a magnet generating an out of plane field with smaller in-plane components and being located below the sensor surface.

The sensor surface of the system can comprise an analyte-specific probe or an analyte-analogue.

The dimension of the sensor surface located between two regions outside the sensor surface can be at least 10, 20, 30, 50 or 100 micrometer.

The analyte-specific probe which can be attached to the sensor surface can be any suitable probe of which an oligonucleotide, an antibody or fragment thereof, a lectin, a pharmaceutical compound, a peptide or a protein are only examples.

The system can also comprise magnetic-particle detection means for detection of a magnetic property of at least one magnetic particle on the sensor surface. The magnetic-particle detection means can detect the magnetic field from the at least one particle, or detects the magnetizability of the at least one particle when subjected to a magnetic detection field. Examples thereof are a magneto-resistive sensor or a Hall sensor.

Another aspect of the invention relates to a disposable cartridge comprising a reaction chamber, a sensor surface having an analyte-specific probe or an analyte-analogue, said reaction chamber comprising at least one region outside the sensor surface and at least one means for generating one or more magnetic fields.

Another aspect of the invention relates to a method for quantifying and/or detecting an analyte, comprising the steps of:

a) providing magnetic particles to a reaction chamber with a surface sensor having an analyte-specific probe and a region outside said sensor surface (all or a part of the magnetic particles can carry an analyte on their surface), b) applying a magnetic field within said reaction chamber having a gradient component parallel to said sensor surface, whereby said magnetic field moves said magnetic particles laterally over said sensor surface toward said region outside said sensor surface, and c) detecting said magnetic particles bound to said sensor surface.

In this method said magnetic field gradient is reversed one or more times before step (c). In such an embodiment the frequency of reversal can be set at any suitable value, e.g. 0.01, 0.05, 0.1, 0.5 or 1 Hz.

In an alternative embodiment the magnetic field gradient is not reversed.

In any embodiment of the method of the present invention one or more magnetic fields can be arranged to move the magnetic particles from a first region outside said sensor surface, to said sensor surface, laterally over said sensor surface, and from said sensor surface to a second region outside said sensor surface.

The first region outside said sensor surface and said second region outside said sensor surface can be the same.

According to another embodiment, said magnetic particles are labeled.

The methods of the present invention can be performed essentially in the absence of the movement of liquid in the reaction chamber.

The present invention also provides methods and sensor systems wherein the step of concentrating magnetic particles comprising an analyte, such as a ligand or a bioactive molecule, on the sensor surface and the step of washing to remove unbound magnetic particles and aspecifically bound particles, are merged. An advantage is to significantly reduce assay time.

It is an advantage of the methods, systems and devices of the present invention that it requires minimal use of reagents.

It is a further advantage of the methods, systems and devices of the present invention that they do not necessarily require a horizontal sensor surface, which can be of interest in the space-management of the devices or laboratories involved.

The present invention discloses a sensing system suitable for the use of magnetic particles (wherein all or a part of the magnetic particles can carry an analyte on their surface), comprising a biochemically active sensor surface with a probe, means to generate a magnetic field that induces a movement of particles over the sensor surface, wherein the induced lateral travel distance of a magnetic particle, with respect to the surface of the sensor is (i) larger than the width of the sensor surface, and (ii) larger than the distance of diffusional transport in absence of a magnetic field. The reaction chamber of the system contains a fluid medium in which the magnetic particles move, can bind to the probes on the sensor surface in case of specific binding and can unbind from the probes on sensor surface in case of aspecific binding.

The present invention permits the design of improved methods and apparatus for the detection of analytes in samples.

The following Figures show embodiments of the present invention in schematic form.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes.

Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The terms or definitions used herein are provided solely to aid in the understanding of the invention.

Definitions

The term "analyte" as used herein refer to a compound in a sample of which the detection of presence and or/concentration is desired.

The term "analyte-specific probe", as used herein, refers to a compound which can bind with the analyte.

The term "reaction chamber" as used herein refers to a region within a device or a cartridge, where different reagents taking part in a reaction are contacted with each other.

The term "sensor surface", as used herein, refers to the part of the reaction chamber, suitable for binding probes, such as analyte-specific probes. Generally, it is also the area where the most important sensitive detection takes place.

The term "region outside the sensor surface" as used herein, refers to a region within a reaction chamber of a device or cartridge, located next to or around the sensor surface, and in the same plane as the sensor surface.

The term "essentially parallel" as used herein refers to movement of particles or to magnetic fields or magnetic field gradients. As the movement of magnetic particles is determined by magnetic field gradients there is often a relationship between the flow and the magnetic filed gradient orientation. With respect to flow, the term refers to orientations corresponding to an angle of less than 45°, or less than 20, less than 10 or less than 5°. With respect to magnetic fields or magnetic filed gradients the term generally only relates to a component of the field or gradient which has an orientation corresponding to an angle of less than 45°, or less than 20, less than 10 or less than 5° with the sensor surface. Notwithstanding the above, the magnetic vector, e.g. magnetic field gradient, may make other angles with the substrate or the sensor surface, e.g. higher than 45° such as 85° or higher.

Typically, in detection and/or quantification methods and systems making use of magnetic particles, the magnetic particles are provided with the analyte (or sample comprising analyte) or a probe, and detection is based on the reaction with a probe or the analyte, respectively, which can be bound to a surface. The present invention provides methods and systems wherein magnetic particles are moved through a reaction chamber, based on the application of one or more magnetic fields, of which the movement is essentially parallel to a sensor surface provided within the reaction chamber.

The force exerted on a magnetic particle by a magnetic field is given by the gradient of the potential energy of the particle in the magnetic field. The magnetic potential energy can be calculated by taking the integral of the magnetization and the field (see for example J. D. Jackson, Classical Electrodynamics, John Wiley & Sons, Inc., 1999). As a result, the force on a magnetic particle relates to the gradient of the magnetic field. In other words, a magnetic particle has a tendency to move from a region of lower to a region of higher magnitude of the magnetic field. Providing a magnetic field with a gradient which is essentially parallel to the sensor surface or has at least a component parallel to the sensor surface allows the movement of the magnetic particles, from an area next to or within the sensor surface, across the sensor surface, so as to allow the molecules present on the magnetic particles to bind with the molecules present on the sensor surface. The lateral movement of particles is generally obtained by a magnetic field with its largest gradient component parallel to the sensor surface. However, any magnetic field gradient differing from perpendicular to the sensor surface can be used as long as it has a component parallel to the sensor surface. In addition, the same or another magnetic field gradient which is essentially parallel to the sensor surface or has at least a component parallel to the sensor surface, ensures removal of the particles not bound, or aspecifically bound to the sensor surface. In this way, the one or more magnetic fields ensure and speed up both the contacting and the washing step and minimizing reagent use.

Alternatively, a field can be generated that also has a gradient component perpendicular to the sensor surface and wherein said component is directed from the reaction chamber (2) to the sensor surface (5). This component keeps the magnetic particles close to the sensor surface and enhances the exposure of the sensor surface to the magnetic particles. Meanwhile, aspecific sticking of particles to the sensor surface can be avoided, e.g. by optimizing the properties of the coating of the sensor surface, the coating of the particles, the fluid composition, and by limiting the size of the perpendicular magnetic force. In addition or as an alternative to this perpendicular magnetic force, other means can be provided to maintain or bring the magnetic particles to the sensor surface, such as a decreased size of the reaction chamber at the sensor surface, or other forces such as a fluid flow or an acoustic or ultrasonic fluid excitation. In a first aspect, the invention provides a system comprising a reaction chamber having a sensor surface and at least one region outside the sensor surface and further comprising one or more means for applying one or more magnetic fields, which is/are placed such that the flow of particles induced by the magnetic field is essentially parallel to the sensor surface and spans the sensor surface and the one or more regions outside the sensor surface.

According to the present invention, the system uses one or more magnetic fields, each of which is generated by one or more magnetic field generating means. Different types of magnetic field generating means are envisaged in the context of the present invention, such as permanent magnets, electromagnets, coils and/or wires. The strength of the magnetic force on the particles should be such that the induced travel distance is larger then the distance traveled without magnetic fields, i.e. the magnetic forces should be dominant over translational Brownian motion. Most particularly, the magnetic field generated by the magnetic field generating means ensure that the travel distance of the magnetic particles (upon activation) of the magnetic field generating means is larger than the size of the sensor surface.

According to the present invention, the magnetic field(s) generated by the one or more magnetic field generating means can be constant, pulsating, or can vary in strength. Moreover, where more than one magnetic field is generated, their exact orientation may be fixed or may vary, provided that the field gradient is essentially parallel to the detection surface or has at least a component parallel to the sensor surface.

Figure 1:
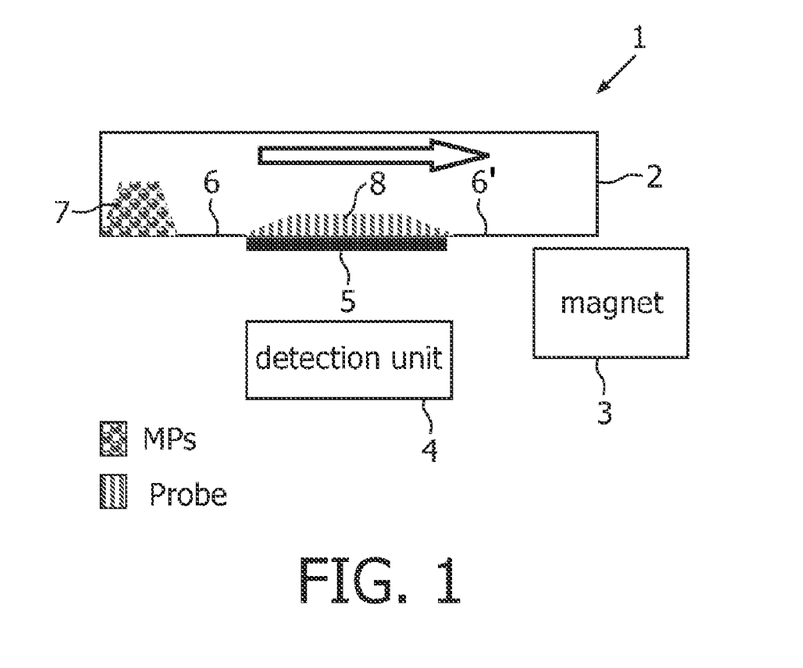
FIG. 1 shows a schematic representation of a magnetic sensor with using one magnet. (MPs: magnetic particles). The arrow indicates the lateral movement of the magnetic particles.

According to one embodiment the system of the present invention contains one single means for generating a magnetic field. An example hereof is shown in FIG. 1. In order to allow removal of the magnetic particles from the sensor surface, the magnetic field generating device is placed such that the magnetic field gradient spans across the sensor surface as well as spanning at least one region outside the sensor surface. According to an alternative embodiment, the magnetic field generating means is placed below the axis of the sensor field, typically just below the plane of the reaction chamber comprising the sensor surface. In these embodiments, the generated magnetic field gradient has a component parallel with the sensor surface as well as perpendicular to the sensor surface. The parallel component drags the magnetic particles over the sensor surface. The magnetic field generating means can be either fixed, spanning the sensor surface and the region outside the sensor surface within its field simultaneously or moveable, sequentially moving the magnetic field over the sensor surface and the region outside the sensor surface. The same effect can be achieved by fixing the magnet and moving the reaction chamber in relation thereto.

According to a particular embodiment, the magnetic field generating means is an electromagnet. This makes it possible to avoid mechanical moving of parts in the device. Alternatively permanent magnets may be arranged to move to and from the reaction chamber.

According to a particular embodiment, the magnetic field generating means is placed below the sensor surface and generates an essentially out-of-plane field with smaller in-plane components.

Figure 2:
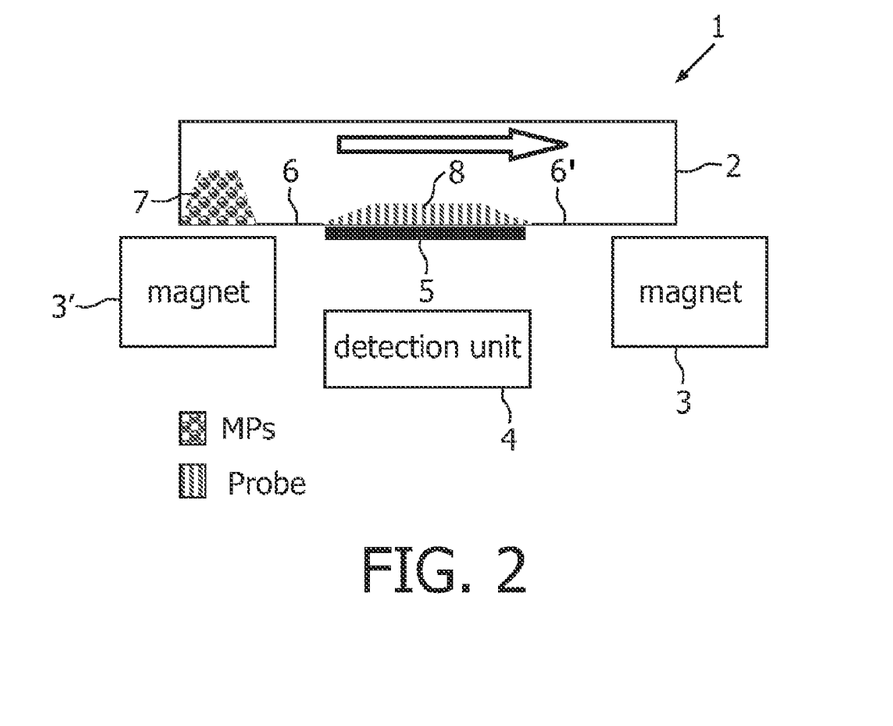
FIG. 2 shows a schematic representation of a magnetic sensor using two magnets. (MPs: magnetic particles) The arrow indicates the lateral movement of the magnetic particles.

According to another embodiment the system of the present invention makes use of more than one magnetic field generating means for generating a magnetic field. A non-limiting embodiment of a system with two magnetic field generating means (3) and (3') is illustrated in FIG. 2. In this illustrated embodiment, the device comprises a reaction chamber with a sensor surface and a first (6) and a second (6') region outside the sensor surface. The alternating activation of both magnets allows the movement of magnetic particles back and forth over the sensor surface from a first region outside the sensor surface (6) to a second region outside the sensor surface (6'). Alternatively, the magnetic field of the magnetic field generating devices spans the sensor surface and one region outside the sensor surface, and the magnetic particles can be moved back and forth between the sensor surface and the two magnetic field generating means. In an alternative embodiment, a magnetic field generating means placed below the sensor surface generating an out-of-plane field is combined with a magnet placed in the plane of the sensor surface for generating an in-plane field.

Yet a further aspect of the present invention provides a system comprising a reaction chamber having a sensor surface and at least one region outside the sensor surface, and the magnetic field generating means are placed in such a way that they allow the generation of magnetic fields of different strength and/or orientation, depending on the assay step. One particular embodiment of this aspect of the invention provides for a system wherein the magnetic field generating means ensure a first magnetic field for the contacting step (movement of the particles towards and/or across the sensor surface) and a second, stronger magnetic field, for the washing step (removal of unbound particles from the sensor surface). According to one embodiment, the device of the invention comprises a first and a second region outside the sensor surface and one magnetic field generating device placed so as to generate a magnetic field between the first region outside the sensor surface and the sensor surface, and a second magnetic field generating device such that the magnetic field between the sensor surface and the second region outside the sensor surface. In another embodiment both magnetic field generating devices are placed so that their respective magnetic field gradients are oriented in opposite directions between a region outside the sensor surface and the sensor surface and alternating activity of the magnetic field generating devices allows movement back and forth to the sensor surface (as described above).

In accordance with a specific embodiment, the second magnetic field can also be used for magnetically-controlled reagent release. For example, magnetic particles are concentrated at a location in the reaction chamber by a concentrating magnetic field, either before or after exposure to the sample fluid. At a controlled time, the concentrating magnetic field is switched off and the magnetic field that generates lateral transport of magnetic particles over the sensor surface is switched on.

According to the present invention, systems are provided which ensure the movement of magnetic particles essentially parallel to the sensor surface in a magnetic field gradient that has at least a component parallel to the sensor surface. It is nevertheless envisaged that the magnetic fields of the present invention can be combined with other forces for moving/immobilizing magnetic particles. Examples of other forces envisaged in this context are other (non parallel) magnetic fields, electrical fields, acoustic forces, hydrodynamic forces, gravitational forces . . . etc. Thus, according to one embodiment, the devices of the present invention comprise magnetic field generating devices which, in addition to the magnetic field gradient which is essentially parallel to the sensor surface, allowing a lateral movement of the particles over the sensor surface, generate magnetic fields that cause movements of the magnetic particles perpendicular to the sensor surface, which can be alternated with the lateral movement. This can be of interest in the context of stirring, to remove unbound or aspecific bound magnetic particles or to improve binding to the sensor surface. Examples of the use of magnetic fields in the context of stirring are described in U.S. Pat. Nos. 5,445,971, 6,548,311, 6,180,418, Perrin et al. (1999), J. Immun. Meth. 224, 77-87; Luxton et al. (2004) Anal. Chem. 76, 1715-1719; and Ferreira et al. (2005) Appl. Phys Lett. 87, 013901. Typically, in the detection and/or quantification devices of the present invention, the sensor surface is placed on the horizontal bottom plane of the reaction chamber. Thus, the magnetic field gradient(s) essentially parallel to the sensor surface are also horizontal. It is however also envisaged that the bottom of the reaction chamber and the sensor surface are inclined, or that the sensor surface in the system is present on a vertical wall of the reaction chamber. In such a configuration one or more magnetic field generating devices can be used in combination with the gravitational force on the magnetic field. According to a particular embodiment, a system is provided comprising a sensor surface on a vertical wall of a reaction chamber and one magnetic field generating device which can be switched on and off. When the magnetic field generating device is switched on, magnetic particles are pulled upwards by the magnetic field generating device, over the sensor surface, allowing specific binding of the magnetic particles to the sensor surface. By switching the magnet off, specifically bound magnetic particles will remain bound to the vertical surface and aspecifically bound particles are pulled downward by gravity. A similar effect can be achieved where the wall of the reaction chamber comprising the sensor surface is inclined. The combination with the gravitational force on the magnetic particles (in the absence of a magnetic field) makes it possible to make one of the steps (such as the contacting step) less stringent. For instance, where the sensor surface is inclined and the magnetic particles can be applied at the top of the inclination, the particles will roll or slide by gravity over the sensor surface. The particles can then be pulled further down or back up the inclination using a magnetic field generating device. This will allow removal of the non-specifically bound particles. As an alternative to gravitational forces which are small, the particles can also be manipulated by a fluid flow or an acoustic or ultrasonic fluid excitation, generating a hydrodynamic shear force to the particles and removing non-specifically bound particles.

Using the magnetic field generating devices, e.g. as known in the art, different methods are available to achieve a maximal interaction of the magnetic particles with probes on the sensor surface. According to one embodiment, the magnetic field(s) is/are applied in such a way that the magnetic particles slide or roll over the magnetic surface. Additionally or alternatively, magnetic field generating devices are used which can be turned on and off. In particular embodiments, one or more magnetic field generating means are provided which can be reversed one or more times. By making use of one or more of these features, the sensitivity of the assays performed with the devices of the present invention can be increased. For instance, by manipulating the magnetic field generating means it is made possible to ensure that the particles can pass one or more times forwards and backwards over the sensor surface, which increases the chance of a magnetic particle to bind to the sensor surface. It is also possible to decrease the size of the reaction chamber near the sensor surface to improve binding of magnetic particles to the sensor surface.

According to the present invention, systems are provided which allow quicker movement of magnetic particles to and from the sensor surface. The sensor surface is typically a specially derivatized surface to which molecules, more particularly probes can be bound. Examples of suitable surfaces include, glass, metal, plastic, an organic crystal or an inorganic crystal (e. g. silicon), an amorphous organic or an amorphous inorganic material (e. g. silicon nitride, silicon oxide, silicon oxinitride, aluminum oxide). Suitable surface materials and linking chemistries are known to the person skilled in the art, and are described for instance in "Diagnostic Biosensor Polymers", by A. M. Usmani and N. Akmal, American Chemical Society, 1994 Symposium Book Series 556, Washington D.C., USA, 1994, in "Protein Architecture, Interfacing Molecular Assemblies and Immobilization Biotechnology", edited by Y. Lvov and H. Mhwald (Marcel Dekker, New York, 2000), in "The Immunoassay Handbook" by David Wild (Nature Publishing Group, London, 2001, ISBN 1-56159-270-6) or "Handbook of Biosensors and Electronic Noses. Medicine, Food and the Environment" by Kress-Rogers (ISBN 0-8493-8905-4). Supports for coupling proteins to coated and uncoated plastic and glass supports are disclosed in Angenendt et al. (2002) Anal Biochem. 309, 253-260. Dufva (2005) in Biomol Eng 22, 173-184, review the methodology to attach oligonucleotides and factors influencing this process.

The invention is generally performed on planar sensor surfaces (e. g. planar glass biochip), but also can be performed in a flow-through system (e. g. flow-through sensors made of porous aluminum oxide, porous silicon, or a porous column containing microparticles).

Typically, where the sensor surface is modified for the binding of probes or analytes thereto, the region outside the sensor surface is a surface which is not so modified. Alternatively, the sensor surface differs from the region outside the sensor surface only in that no molecules have been bound to that area of the reaction chamber surface.

Further aspects of the system of the present invention are mentioned hereafter. The system of the invention will usually comprise one or more inlet means for introducing sample, magnetic particles or reagents into the reaction chamber, and optionally an outlet means for removing reagents, reaction waste, and optionally, magnetic particles, from the reaction chamber. These can optionally be coupled to sources comprising each of the reagents. According to one embodiment, an inlet means for sample and/or magnetic particles directs the sample and/or magnetic particles to a region outside the sensor surface or directly to the sensor surface. Additionally or alternatively, one or more inlet and outlet means are provided so as to ensure the direct delivery of the sample and/or magnetic particles and/or other reagents or buffers in the reaction chamber. The different inlet and/or outlet means can be connected to connection means such as valves and tubing, which can be driven by pumps.

As detailed above, the devices of the invention comprise, within a reaction chamber, one or more regions outside the sensor surface. This/these regions can be used to collect the particles at the start of the assay, or to collect the non-bound particles when the 'washing' step is being performed. For instance, the magnetic field generated in the device of the invention may span, besides the sensor surface, one or more regions outside the sensor surface. The magnetic field can be such that the unbound particles are pulled back out of the sensor surface and into a region outside the sensor surface. In some embodiments the physical separation between the bound and the unbound magnetic particles allows the detection of both fractions, providing a further control on the method.

As indicated above, the devices of the present invention are envisaged to contain one or more regions outside the sensor surface. In one embodiment, the reaction chamber comprises at least one region outside the sensor surface which is adapted to the collection of the magnetic particles prior to the assay, e.g. by the presence of an indentation or small crevices, or by the presence of a controllable magnetic field generating means. Such dedicated regions can also be provided within the sensor surface.

According to one embodiment, the reaction chamber comprises a first region outside the sensor surface where the particles reside before the assay and a second region outside the sensor surface, to which the unbound particles are moved (these regions being e.g. on opposite sites of the reaction chamber as depicted in FIG. 1). In other embodiments, such as depicted in FIG. 2, the magnetic particles are moved back and forth from a region outside the sensor surface to the sensor surface. Optionally, the magnetic particles can be moved back and forth several times prior to the detection step.

The system of the present invention either further comprises or is used in combination with a detection means, capable of detecting the binding of magnetic particles to the sensor surface. Detection of the bound magnetic particles on the sensor surface can be done by various means, either based on the properties of the magnetic particles themselves or using a label. The label can be attached to the magnetic particles, or can be bound to or incorporated into the analyte.

Accordingly, the detection means present in or used in combination with the systems of the present invention are detection means capable of detecting the relevant signal such as, but not limited to, a magnetic signal, magnetoresistance, a Hall effect, an optic signal (reflection, absorption, scattering, fluorescence, chemiluminescence, RAMAN, etc.), an acoustical signal (quartz crystal microbalance (QCM), surface acoustic waves (SAW), Bulk Acoustic Wave (BAW) etc.). These may be generated by liposomes, micelles, bubbles, microbubbles, microspheres, lipid-, or polymer coated bubbles, microbubbles and/or microspheres, microballoons, aerogels, clathrate bound vesicles, and the like. Such vesicles may be filled with a liquid, a gas, a gaseous precursor, and/or a solid or solute material.

Typical labels useful in the context of the present invention are those labels which are classically used in in vitro assays such as, but not limited to, chromophoric groups, radioactive labels, electroluminescent, chemiluminescent, phosphorescent, fluorescent or reflecting labels.

Magnetic particles used in the present invention can be completely inorganic or can be a mixture of an inorganic and an organic material (e.g. a polymer). Accordingly, labels can be attached via the inorganic or via the organic component at the outside or can be incorporated into the particle.

Magnetic particles are widely used in biological analysis, e. g. in high-throughput clinical immunoassay instruments, sample purification, cell extraction, etc. Several diagnostic companies (Roche, Bayer, Johnson & Johnson, Abbott, BioMerieux, etc.) fabricate and sell reagents with magnetic particles, e.g. for immunoassays, nucleic-acid extraction, and sample purification. Magnetic particles are commercially available in various sizes, ranging from nanometers to micrometers. For attachment or binding of the particles of the invention to the bioactive molecules, the particles may carry functional groups such as hydroxyl, carboxyl, aldehyde or amino groups. These may in general be provided, for example, by treating uncoated monodisperse, superparamagnetic particles, to provide a surface coating of a polymer carrying one of such functional groups, e. g. polyurethane together with a polyglycol to provide hydroxyl groups, or a cellulose derivative to provide hydroxyl groups, a polymer or copolymer of acrylic acid or methacrylic acid to provide carboxyl groups or an aminoalkylated polymer to provide amino groups. U.S. Pat. No. 4,654,267 describes the introduction of many such surface coatings. Other coated particles may be prepared by modification of the particles according to the U.S. Pat. Nos. 4336173, 4459378 and 4,654,267. For example, macroreticular porous polymer particles, prepared from styrene-divinylbenzene and with a diameter of 3.15 um were treated with $HNO_3$ to introduce-$NO_2$ groups at the surface of the pores. Then the particles were dispersed in an aqueous solution of Fe. The $Fe^{2+}$ is oxidized by the $NO_2$ groups which leads to precipitation of insoluble iron oxy-hydroxy compounds inside the pores. After heating the iron exists as finely divided grains of magnetic iron oxides throughout the volume of the porous particles The $NO_2$ groups are reduced by the reaction with Fe to $NH_2$ groups. To fill up the pores and to introduce the desired functional groups at the surfaces, different monomers are caused to polymerize in the pores and at the surface. In the case of a preferred type of particle, the surface carries-OH groups connected to the polymeric backbone through $(CH_2CH_2O)$ 8-10 linkages. Other preferred carry —COOH groups obtained through polymerization of methacrylic acid. For example, the $NH_2$ groups initially present in the particles may be reacted with a diepoxide as described in U.S. Pat. No. 4,654,267 followed by reaction with methacrylic acid to provide a terminal vinyl grouping. Solution copolymerization with methacrylic acid yields a polymeric coating carrying terminal carboxyl groups. Similarly, amino groups can be introduced by reacting a diamine with the above product of the reaction with a diepoxide, while reaction with a hydroxylamine such as aminoglycerol introduces hydroxy groups.

The coupling of a bio active molecule to a particle can be irreversible but can also be reversible by the use of a linker molecule for the crosslinking between particle and bioactive molecule. Examples of such linkers include peptides with a certain proteolytic recognition site, oligonucleotide sequences with a recognition site for a certain restriction enzyme, or chemical reversible crosslinking groups as those comprising a reducible disulfide group. A variety of reversible crosslinking groups can be obtained from Pierce Biotechnology Inc. (Rockford, Ill., USA).

According to a particular embodiment, the sensor of the detection unit is integrated into the reaction chamber (e.g. magnetoresistive sensor is integrated), which can be provided as a disposable cartridge. Alternatively, the sensor is provided as separate part from the reaction chamber (e.g. optical unit). In this embodiment, the reaction chamber optionally comprises a detection window, which allows the detection of the signal of the magnetic particles and/or labels bound to the sensor surface. The location of the detection window is of course determined by the location of the sensor surface and the detection means. Most particularly, the detection window is opposite to the sensor surface. Alternatively, sensor surface of the reaction chamber is provided on the detection window. Where the detection is based on magnetic field or optical methods, the material of the reaction chamber may render the provision of a specific detection window superfluous. Additionally or alternatively, the systems of the present invention provide for the detection of magnetic particles in a region outside the sensor surface. This can be of interest in the context of controls or validation measurements (see below), or where the detection method is based on a competitive binding at the detection surface. Where appropriate, the systems of the present invention are thus provided with an additional detection window and/or an additional detection means or a means which can simultaneously or sequentially detect a signal both on the sensor surface and in a region of the reaction chamber outside the sensor surface.

Typically the system of the present invention is a single-chamber (bio)sensor, with low reagent use and small required sample volume. A (bio)sensor in accordance with the present invention comprises can be operated with a minimum of equipment, washing steps and buffers.

Another aspect of the present invention provides an optionally disposable cartridge comprising a reaction chamber having a sensor surface and at least one region outside the sensor surface. The disposable cartridge can further comprise magnetic particles integrated therein or these can be provided separately. The material of the cartridge is such that magnetic fields can be generated therein. For example, the cartridge is made of glass or a synthetic material, such as plexiglass [poly(methy)methacrylate] or clear PVC (polyvinyl chloride) or PC (polycarbonate) or COP (e.g. Zeonex) or PS (polystyrene).

The cartridge can further comprise at least one magnetic field generating device or a part thereof, which can be used in the generation of a magnetic field gradient essentially parallel to the detection surface within the reaction chamber or having at least a component parallel to the detection surface.

According to yet another aspect the invention provides methods whereby the systems and/or cartridges of the present invention are used for the detection and/or quantification of analytes. The methods of the present invention thus generally comprise providing within a reaction chamber having a detection surface and a region outside the detection surface, an analyte-specific probe, magnetic particles and a sample believed or known to comprise the analyte and applying at least one magnetic field gradient to the particles, which is essentially parallel to the sensor surface or has at least a component parallel to the sensor surface. The methods performed in accordance with the present invention are rapid, sensitive, and robust.

The methods of the present invention are applicable in the detection of any molecule, more particularly biomolecules such as DNA, RNA, proteins, carbohydrates, lipids and organic anabolites or metabolites. The nature of the sample comprising the analyte to be detected is not critical and can be for instance any sample of a living or dead organism (body fluid such as, but not limited to blood or urine, hair, stool, etc.), an environmental sample (water, soil, plant material), food or feed products or products used in the manufacturing thereof, a sample of a chemical reaction process etc . . . . The detection can be performed on a sample which is the result of a pre-processing step such as a semi-purification, purification, semi-purification and/or amplification of the analyte. According to a particular embodiment, the analyte is a single stranded nucleotide sequence, which has been amplified using PCR.

The methods of the present invention provide for a detection of an analyte based on the reaction/binding of the analyte with an analyte-specific probe. Typical specific interactions include DNA/DNA or DNA/RNA binding, protein/protein, protein/DNA and protein/carbohydrate interactions antibody/antigen interactions, receptor/ligand binding. Also synthetic molecules can be used to detect an analyte (e.g. enzyme inhibitors, pharmaceutical compounds, lead compounds isolated from library screenings). Accordingly, examples of analyte-specific probes include but are not limited to oligonucleotides, antibodies, enzyme substrates, receptor ligands, lectins etc . . . . Examples of envisaged sensor surface and analyte interactions are a sensor surface comprising antibody probes to detect antigens in a sample or antigens attached as probe to the sensor surface for the detection of antibodies in a sample.

According to a particular embodiment of the invention, the analyte-specific probe is an analyte-specific oligonucleotide, i.e. an oligonucleotide comprising a sequence which is complementary to a sequence specific for the analyte.

Different assay principles are envisaged in the detection methods of the invention. In one embodiment, the detection and/or quantification method used is a direct detection method. For example, the analyte present in the sample is bound to magnetic particles, which are moved across a sensor surface comprising an analyte-specific probe and the signal generated by the particles bound to the sensor surface is directly proportionate to the number of magnetic particles bound to the sensor surface, and thus to the presence (and/or amount) of analyte present in the sample. Alternatively the detection can be based on competitive binding of the analytes to the sensor surface. For example, the sensor surface is first provided with magnetic particles bound to the analyte-specific probe on the sensor surface through an analyte-like compound (weak binding to the sensor surface) and upon contacting with magnetic particles to which the analyte is linked, displacement of the analyte-like compound takes place. Where the magnetic particles comprising the analyte-like compound are labeled, the signal is inversely proportionate to the amount of analyte in the sample. Alternatively, the signal of the magnetic particles not bound to the sensor surface can be measured in a region outside the sensor surface. In other embodiments, the detection of the analyte is envisaged to require the addition of further reagents such as secondary antibodies, labels, substrates etc . . . . More specifically for specific analytes (large molecules, e.g. proteins, possessing at least two epitopes) sandwich assays can be envisaged. In a sandwich assay, molecules of interest (proteins) from an applied sample fluid are trapped ('sandwiched') between a probe (a first antibody) on a biologically active sensor surface and a biologically active molecule (a second antibody) with a label (a magnetic particle). Although the molecule of interest is the protein sandwiched between the two antibodies, the antibody on the sensor surface and the protein act as the probe and the labeled second antibody as an analyte according to the terminology of the present invention. In another embodiment of a sandwich assay, the antibody on the sensor surface acts as the probe and the labeled second antibody and the protein act as an analyte according to the terminology of the present invention.

Thus, as indicated above in a particular embodiment of the methods of the invention, one or more analyte-specific probes are bound to the sensor surface and the analyte is provided on the magnetic particle. In this embodiment, the analyte is bound to the magnetic particle either directly (non-specific adsorption of the sample or a pre-processed fraction thereof to the magnetic particle) or specifically (through the use of an analyte-specific probe, attached to the surface of the molecule).

The magnetic particles suitable for use in the methods and devices of the present invention are known to the skilled person. Magnetic particles of different size (10 nm to 5 μm, typically between 50 nm and 1 μm), shape (spheres, spheroids, rods), composition (see before in this application), and magnetic properties (magnetic, paramagnetic, superparamagnetic, ferromagnetic, i.e any form of magnetism which has a magnetic dipole in a magnetic field, either permanently or temporarily) have been described. It is envisaged that different types of magnetic particles, e.g. with different magnetic and/or optical properties can be used simultaneously within one reaction chamber (magnetic particle multiplexing).

Attachment of the analytes or probes to the surface of magnetic particles can be performed by methods described in the art, as described above in this application.

According to one embodiment, the invention provides methods for the detection and/or quantification of an analyte, comprising the step of contacting a sample comprising an analyte with magnetic particles and subjecting the magnetic particles to a magnetic field in a reaction chamber (2) with a sensor surface (5) comprising an analyte-specific probe (8). The step of subjecting the magnetic particles to a magnetic field is performed such that the magnetic particles are moved laterally over the sensor surface (5), whereby the movement of magnetic particles (7) spans between at least one region outside the sensor surface (6) and the sensor surface, and detecting the signal generated by the binding of the magnetic particles to the sensor surface. Depending on whether or not the magnetic particles are present within the reaction chamber, the method can further comprise the step of introducing magnetic particles within the reaction chamber. Typically, the magnetic particles are applied to first a region outside the sensor surface and, the one or more magnetic fields ensure the movement of the particles from the first region outside the sensor surface to the sensor surface and laterally over at least part of the sensor surface (5). Alternatively, the magnetic particles are introduced into the reaction chamber in a random fashion (e.g. magnetic particles, to which analyte has been bound are applied to a reaction chamber and than shaken) and magnetic forces can be used to attract the magnetic particles to the sensor surface. In yet another alternative embodiment the magnetic particles are introduced into the reaction chamber directly on the sensor surface.

It is envisaged that the methods of the present invention are performed using reaction chambers comprising an analyte-specific probe bound thereto. Alternatively however, the methods of the present invention further encompass the step of providing an analyte-specific probe on the sensor surface. Depending on the nature of the material of the sensor surface, the binding of the analyte-specific probe to the sensor surface will require a specific chemical reaction and/or a blocking step.

In the methods of the present invention the binding of the analyte to the magnetic particles (7) is either performed within or outside the reaction chamber. Thus in a particular embodiment, the reaction chamber comprises magnetic particles in a region outside the sensor surface and the methods further comprise the step of introducing the sample into the reaction chamber in the same region outside the sensor surface thereby contacting the sample with the magnetic particles. Alternatively, the methods of the invention comprise the step of contacting the sample with the magnetic particles outside the reaction chamber and introducing the magnetic particles to which the sample/analyte has bound in the reaction chamber.

According to a particular embodiment, the one or more magnetic fields further ensure the movement of the particles not bound to the sensor surface to a second region (6') outside the sensor surface (5). Optionally the first and the second regions (6, 6') outside the sensor surface (5) are the identical (i.e., movement is back and forth).

As detailed above, the movement of the magnetic particles can be ensured using one magnetic field. Alternatively, the methods of the invention comprise the generation of different magnetic field gradients essentially parallel to the detection surface or having at least a component parallel to the detection surface for the contacting of the analyte with the sensor surface (movement of particles towards sensor surface) and the removal of the unbound magnetic particles (movement of particles away from sensor surface). Moreover the essentially parallel magnetic field gradients or having at least a parallel component can be alternated or combined with other movements of the particles generated by e.g. magnetic, electrical, hydrodynamic, sonic, or gravitational forces in the context of washing steps, introduction of the magnetic particles into the reaction chamber and/or removal of the particles from the reaction chamber (as described for the systems of the invention above).

The methods of the present invention involve the contacting of sample with magnetic particles and the movement of particles within a reaction chamber. Magnetic particles can be part of a fluid reagent or of a dry reagent. Besides magnetic particles, the reagent can for example contain buffer salts, detergents, biomolecules that assist in the biological interactions, etc. These steps can be performed in a liquid, which is any liquid compatible with the reagents used (i.e. analyte, analyte-specific probe, label), such as standard buffers, or minimally pre-treated or even pure sample (e.g. blood or saliva). Liquid can be introduced in the reaction chamber for rinsing purposes. A liquid current can also be applied to provide a flow contrary to the movement of the magnetic particles. Such a flow can be applied with pumps but also without pumps using an electric field to generate electroosmosis.

Alternatively, the methods are performed with a minimum amount of liquid at the detection surface and optionally the region outside the detection surface. To avoid spreading of irrelevant sample components which can interfere with binding or detection, the sample can be applied in a solution or matrix which avoids such movement, such as glycerol or in a gel which disintegrates in the reaction chamber.

Upon application of a magnetic field only the magnetic particles will move while buffer, and other components of the sample which can interfere with binding or detection (e.g. traces of a body fluid such as blood or urine) remain at the site of application. The presence of the liquid will influence the strength of the magnetic field required to move the particles For example, the flow resistance is lower in a clean buffer than in a sample with high viscosity, e.g. saliva.

When the magnetic particles are supplied in a small volume at a distance removed from the sensor surface, no or minimal interchange by diffusion will occur between the liquid wherein the magnetic particles are supplied and the liquid which is present at the sensor surface.

The methods of the present invention further comprise a detection step, which allows the detection and/or quantification of the magnetic particles to the sensor surface. The detection step is ensured using one or more detection means as described for the systems of the invention above.

According to the present invention, the binding between, e.g. an analyte present on the surface of a magnetic particle and an analyte-specific probe on the sensor surface of the reaction chamber ensures that these magnetic particles are immobilized on the sensor surface. According to one embodiment the magnetic field of the magnetic particles bound to the sensor surface through the analyte can be used to detect the presence of the particle on the sensor surface and consequently of the analyte attached to the magnetic particle. In addition or alternatively, the detection of a magnetic particle is performed visually by the presence of the particle itself or by labels such as chromophoric groups in or on the particle.

According to a particular embodiment, the sensor surface comprises one analyte-specific probe. Alternative embodiments are also envisaged whereby a variety of analyte-specific probes are arrayed on the sensor surface to allow simultaneous detection of different compounds in a sample. (sensor multiplexing) (a sensor array with different capture molecules). Another modification is chamber multiplexing. Herein a system has multiple reaction chambers. In one embodiment, the sample is spread over different chambers to run different assays in parallel. Alternatively, magnetic particles which passed over a first sensor surface in a first reaction chamber are further transported to a next reaction chamber wherein they can react with probes on a next surface sensor (system with several reaction chambers).

As detailed above, the methods of the present invention involve the use of a reaction chamber comprising a sensor surface and at least one region outside the sensor surface.

In the methods and devices of the present invention, magnetic particles are concentrated near the sensor surface, thereby reducing the time needed to allow binding between probe an analyte and increasing the chance of the binding of a rare analyte to a probe. During the flow-over transportation, the magnetic particles have a dynamic movement (driven by a magnetic field gradient, magnetophoresis), combined with translational and rotational diffusion of the particles.

Non-homogeneous magnetic particle solutions, e.g. due to a large size distribution of particles or the presence of clusters of sticking particles, can cause large signal variations and signal offsets in standard assays with magnetic particles. The methods performed in accordance with the present invention are to a large degree not influenced by the presence of a fraction of large magnetic particles or magnetic particle clustering, due to the lateral magnetic force on the particles, which is higher for particles with higher magnetization. This stronger magnetophoretic force gives the larger particles a higher velocity, which reduces the residence time near to the sensor surface. In addition, larger particles have a higher average travel height above the sensor surface due to the strong hydrodynamic friction near to the surface, which further reduces the number of collisions with the sensor surface. As a result, larger magnetic units will have a reduced interaction with the sensor surface compared to smaller particles. In the methods of the present invention, the binding of large magnetic particles or large clusters to the sensor surface is inherently suppressed, which makes the detection more reliable. Magnetic particles can also temporarily form multi-particle structures in a magnetic field, due to dipole-dipole interactions. For example, chains of particles can form, oriented along the lines of the magnetic field. Such structures can change or dissemble when the field is removed and/or when the chain is excited by other forces. In the method of the present invention, the lateral movement of particles and multi-particle structures provides a source of excitation. The movement along the surface causes a dynamic process of continuous assembly/disassembly, refreshment, and reformation of multi-particle structures. As a result, there is good contact between the particles and the sensor surface.

The system and methods described in the present invention can be used as rapid, robust, and easy to use point-of-care biosensors for small sample volumes. The reaction chamber can be a disposable item to be used with a compact reader, containing the one or more magnetic field generating means and one or more detection means.

Also, the systems and methods of the present invention can be used in automated high-throughput testing for centralized laboratories. In this case, the reaction chamber is e.g. a well plate or cuvette, fitting into an automated instrument. When applied in e.g. immunoassays, a minimum number of fluid manipulation steps are needed, incubation occurs at high speed and washing steps are reduced to a minimum with a minimal fluid waste.

Other arrangements for embodying the invention will be obvious for those skilled in the art.

It is to be understood that although preferred embodiments, specific constructions and configurations, as well as materials, have been discussed herein for devices and methods according to the present invention, various changes or modifications in form and detail may be made without departing from the scope and spirit of this invention. The invention is illustrated by the Examples provided below which are to be considered for illustrative purposes only and the invention is not limited to the specific embodiments described therein.

EXAMPLES

Example 1: Magnetic Binding Assay

Figure 3:
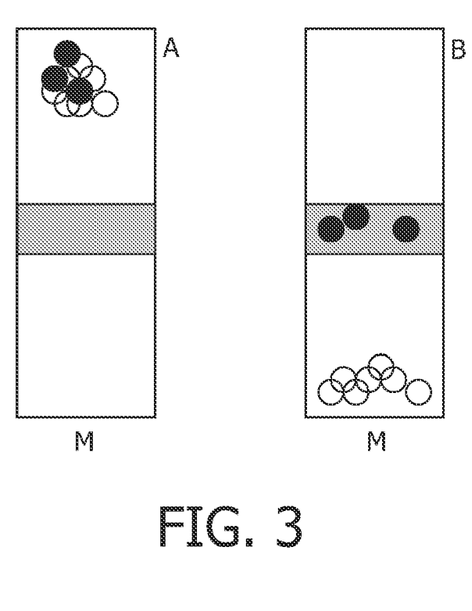
FIG. 3 shows the magnetic movement towards a magnet (M) of uncoated magnetic particles (white circles) and antibody coated magnetic particles (black circles) over an antigen coated (grey part) sensor surface.

A region of a polystyrene reaction chamber is coated with morphine coupled to BSA (grey zone in FIG. 3). Afterwards the remainder of the reaction chamber is coated with BSA to avoid aspecific binding to polystyrene. A solution containing magnetic particles coated with anti-morphine Ab (200 nm Protein G coated magnetic particles) (black circles in FIG. 3) and magnetic particles without antibody (white circles in FIG. 3) is applied to a region outside the sensor surface (top part of FIG. 3A). The amount of morphine on the sensor surface is sufficient to bind all antibody coated magnetic particles.

To avoid any movement of the magnetic particles on the reaction chamber, they are applied to the reaction chamber in a solution of low melting agarose. After application the reaction chamber is filled with buffer. An electromagnet (M in FIG. 3) is placed under the reaction chamber at the opposite end from the place where the magnetic particles were applied. The configuration of the assay before a magnetic field is applied is shown in FIG. 3A.

The reaction chamber is heated to about 40° C. which releases the magnetic particles from the agarose gel. The electromagnet is switched on and generates a magnetic field, which draws the magnetic particles over the sensor surface. Particles with antibodies bind to the morphine, while the remainder travels further towards the electromagnet (FIG. 3B). The magnetic particles which are collected at the electromagnet are assayed for binding to morphine. This control shows the efficacy of the assay.

Example 2: Competition Assay

A pilot experiment was performed using morphine as a detection agent. Morphine is a small molecule, with only one epitope, so a competitive assay has to be performed to indicate the amount of morphine in a sample. On a polystyrene surface (96 wells titre plate), 1 µl of BSA-morphine (1 mg/ml in phosphate buffered saline (PBS)) was spotted in a corner of each well and dried [morphine-3-glucoronide was coupled in excess BSA via its lysine residues]. After coating, the wells were blocked with 10 mg/ml BSA+0.65% Tween-20 in PBS for 1 hour. Then, the blocking solution was discarded and 10 mg/ml BSA+0.65% Tween-20 in PBS containing anti-morphine Ab coated magnetic particles (200 nm Protein G coated magnetic particles) were applied to the wells (1:10 dilution of magnetic particles, total amount of solution was 50 µl. The titer plate was placed on a magnet and after 1 minute pictures were taken (FIG. 4) The magnetic particles are detected by optical reflection. During this period magnetic particles move over the place where the morphine is spotted. The magnetic particles which are specifically bound via the antibodies to the morphine, remain located at the place where the morphine was applied (arrow 1) (FIG. 4 top panel), while the remaining magnetic particles (having no antibodies or having antibodies which did not react with morphine) moved towards the magnet (arrow 2).

When sufficient morphine (5 or 100 ng/ml in a microtiter well) was added to the antibody-coated magnetic particles prior to the application to the titre plate, antibodies were saturated with morphine and could only bind in a non specific way to the wells of the plate. The middle and bottom panel of FIG. 4 show that such interactions are not sufficient to elicit a visible spot of bounding magnetic particles.

Figure 4:
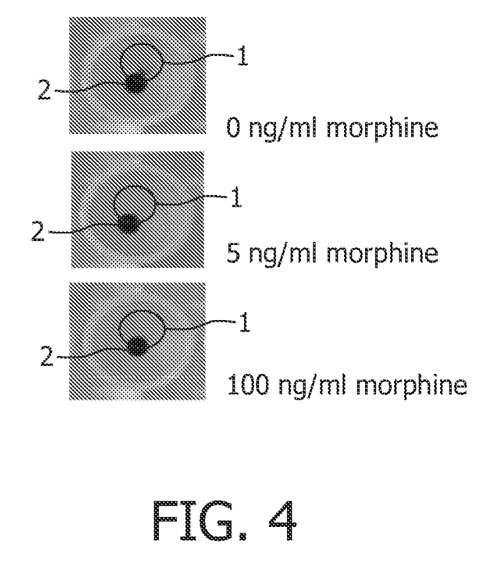
FIG. 4 shows the magnetic movement of magnetic particles with anti-morphine antibody over a morphine coated sensor surface.
Figure 5:
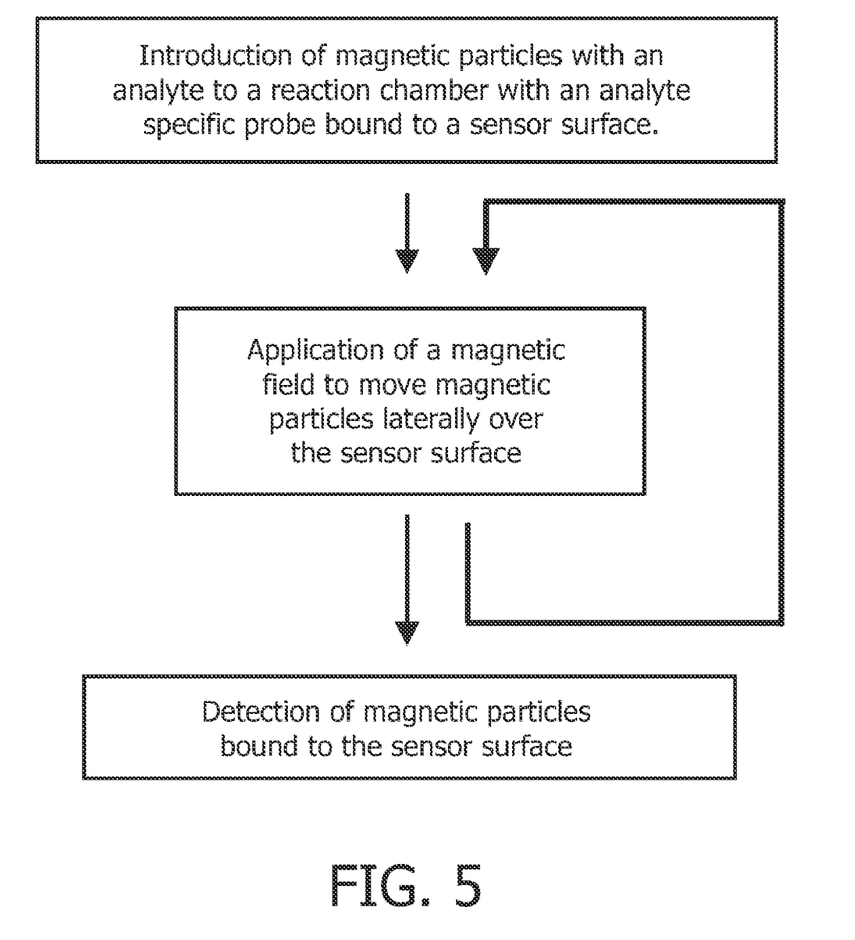
FIG. 5 shows a flowchart of the method for laterally moving magnetic particles over a sensor surface.

FIG. 4 shows that morphine in a sample, already at 5 ng/ml, prevents the binding of the magnetic particle coupled antibodies to the spotted morphine. There are not enough magnetic particles bound to elicit a visible spot of bound magnetic particles.

The invention claimed is:

1. A method, comprising:
providing magnetic particles to a first region of a reaction chamber, the reaction chamber comprising a sensor surface and a second region, the sensor surface having an analyte-specific probe or an analyte-analogue, wherein the first region and the second region are both outside the sensor surface at opposite ends of the reaction chamber and in a plane of the sensor surface, the sensor surface located between the first region and the second region, and wherein a first portion of the magnetic particles comprises an analyte and a second portion of the magnetic particles do not comprise the analyte;
applying, during a first period of time, a first magnetic field gradient using a first magnet, wherein the first magnet is outside the reaction chamber below the plane of the sensor surface, wherein the first magnetic field gradient has a gradient with a component perpendicular to the sensor surface and directed toward the second region, wherein the first magnetic field gradient removes all the magnetic particles from the first region laterally over the sensor surface above a plane of the sensor surface, wherein some or all of the first portion of the magnetic particles becomes bound to the sensor surface, and wherein the second portion and any remaining magnetic particles of the first portion move to the second region;
subsequent to the first period of time, applying, during a second period of time, a second magnetic field gradient within the reaction chamber using a second magnet, wherein the second magnet is outside the reaction chamber below the plane of the sensor surface, wherein the second magnetic field gradient has a component essentially parallel to the sensor surface, wherein the second magnetic field gradient removes all the magnetic particles from the second region laterally over the sensor surface above a plane of the sensor surface, wherein some or all of the remaining first portion of the magnetic particles becomes bound to the sensor surface, wherein the second portion and any still remaining first portion of the magnetic particles move to the first region, and wherein the second period of time starts after the first period of time; and detecting the first portion of magnetic particles bound to the sensor surface, wherein the first and second magnets are confined to the ends of the reaction chamber such that the first and second magnets do not overlap the sensor surface and no magnet is located directly beneath the sensor surface.

2. The method of claim 1, further comprising:
repeating at least once the applying of the first and second magnetic field gradients at a reversal frequency.

3. The method of claim 2, wherein the reversal frequency is greater than 0 Hz and less than 0.1 Hz.

4. The method of claim 1, wherein the second magnetic field gradient includes applying the second magnetic field gradient in one direction.

5. The method of claim 1, wherein applying the first and second magnetic field gradients includes applying each of the first and second magnetic field gradients once.

6. The method of claim 1, further comprising:
providing a dedicated area on the first region outside the sensor surface; and
the dedicated area collecting the magnetic particles prior to the assay.

7. The method of claim 6, further comprising:
using an inlet, introducing the magnetic particles into the reaction chamber.

8. The method of claim 1, wherein applying the first magnetic field gradient or the second magnetic field gradient includes transporting the magnetic particles a first distance, wherein the first distance is greater than a second distance.

9. The method of claim 8, further comprising obtaining the second distance by Brownian motion.

10. The method of claim 1, further comprising at least one of the first and second magnets generating an out of plane field with smaller in-plane components.

11. The method of claim 1, wherein a dimension of the sensor surface located between the first region and the second region is at least between 10 micrometers and 30 micrometers.

12. The method of claim 1, wherein current carrying conductors suitable for attracting the magnetic particles to the sensor surface or to a region outside the sensor surface are absent.

13. The method of claim 1, wherein the analyte-specific probe is selected from the group consisting of: an oligonucleotide, an antibody or fragment thereof, a lectin, a pharmaceutical compound, a peptide, and a protein.

14. The method of claim 1, further comprising:
using a magnetic-particle detector, detecting a magnetic field from a magnetic particle or detecting magnetizability of the magnetic particle when subjected to a magnetic detection field.

15. The method of claim 14, wherein the magnetic particle is bound to the sensor surface.

16. The method of claim 14, wherein the magnetic-particle detector comprises a magneto-resistive sensor or a Hall sensor.

17. The method of claim 1, wherein generating the first magnetic field gradient during the first period of time includes generating the first magnetic field gradient while the second magnetic field gradient is switched off.

18. The method of claim 1, wherein generating the second magnetic field gradient during the second period of time includes generating the second magnetic field gradient while the first magnetic field gradient is switched off.

19. The method of claim 1, wherein the second magnetic field gradient is stronger than the first magnetic field gradient.

* * * * *